(12) United States Patent
Dang

(10) Patent No.: US 7,429,692 B2
(45) Date of Patent: Sep. 30, 2008

(54) SUCROSE SYNTHASE 3 PROMOTER FROM RICE AND USES THEREOF

(75) Inventor: David Vandinh Dang, Oak Park, CA (US)

(73) Assignee: Ceres, Inc., Thousand Oaks, CA (US)

(*) Notice: Subject to any disclaimer, the term of this patent is extended or adjusted under 35 U.S.C. 154(b) by 319 days.

(21) Appl. No.: 11/274,890

(22) Filed: Nov. 15, 2005

(65) Prior Publication Data

US 2006/0112445 A1    May 25, 2006

Related U.S. Application Data

(63) Continuation-in-part of application No. 10/966,482, filed on Oct. 14, 2004.

(51) Int. Cl.
- C12N 15/82 (2006.01)
- A01H 5/00 (2006.01)
- C07H 21/04 (2006.01)

(52) U.S. Cl. .................. 800/287; 800/278; 800/285; 800/286; 800/298; 800/295; 435/419; 435/468; 536/24.1; 536/24.5

(58) Field of Classification Search .................. None
See application file for complete search history.

(56) References Cited

U.S. PATENT DOCUMENTS

| | | | |
|---|---|---|---|
| 4,987,071 A | 1/1991 | Cech et al. | |
| 5,004,864 A | 4/1991 | Robertson et al. | |
| 5,034,323 A | 7/1991 | Jorgensen et al. | |
| 5,204,253 A | 4/1993 | Sanford et al. | |
| 5,254,678 A | 10/1993 | Haseloff et al. | |
| 5,321,020 A | 6/1994 | Jasys | |
| 5,538,880 A | 7/1996 | Lundquist et al. | |
| 5,591,616 A | 1/1997 | Hiei et al. | |
| 5,702,933 A | 12/1997 | Klee et al. | |
| 5,706,603 A | 1/1998 | Bergquist et al. | |
| 6,011,200 A | 1/2000 | Dellaporta et al. | |
| 6,013,863 A | 1/2000 | Lundquist et al. | |
| 6,255,561 B1 | 7/2001 | Kossman et al. | |
| 6,320,106 B1 | 11/2001 | Ertl et al. | |
| 6,326,527 B1 | 12/2001 | Kirihara et al. | |
| 6,329,567 B1 | 12/2001 | Jofuku et al. | |
| 6,329,571 B1 | 12/2001 | Hiei | |
| 6,355,862 B1 | 3/2002 | Handa et al. | |
| 6,423,885 B1 | 7/2002 | Waterhouse et al. | |
| 6,429,356 B1 | 8/2002 | Shewmaker | |
| 6,444,469 B1 | 9/2002 | Dellaporta et al. | |
| 6,452,067 B1 | 9/2002 | Bedbrook et al. | |
| 6,455,688 B1 | 9/2002 | Slabas et al. | |
| 6,459,019 B1 | 10/2002 | Falco et al. | |
| 6,573,099 B2 | 6/2003 | Graham | |
| 6,753,139 B1 | 6/2004 | Baulcombe et al. | |
| 6,777,588 B2 | 8/2004 | Waterhouse et al. | |
| 6,897,359 B2 | 5/2005 | Thompson et al. | |
| 6,900,368 B2 | 5/2005 | Thompson et al. | |
| 6,906,244 B2 | 6/2005 | Fischer et al. | |
| 6,940,001 B1 | 9/2005 | Landschuetze | |
| 2002/0049996 A1 | 4/2002 | Kaeppler et al. | |
| 2003/0074687 A1 | 4/2003 | Scott | |
| 2003/0126642 A1 | 7/2003 | Fischer et al. | |
| 2003/0135890 A1 | 7/2003 | Fischer et al. | |
| 2003/0175783 A1 | 9/2003 | Waterhouse et al. | |
| 2003/0180945 A1 | 9/2003 | Wang et al. | |
| 2004/0053876 A1 | 3/2004 | Turner et al. | |
| 2004/0214330 A1 | 10/2004 | Waterhouse et al. | |
| 2005/0091711 A1 | 4/2005 | Ito et al. | |
| 2005/0204429 A1 | 9/2005 | Penell et al. | |
| 2006/0008816 A1 | 1/2006 | Lu et al. | |

FOREIGN PATENT DOCUMENTS

| | | | |
|---|---|---|---|
| EP | 0 270 822 | 6/1988 | |
| EP | 0 117 618 | 7/1988 | |
| EP | 0 242 246 | 11/1992 | |
| EP | 0 344 029 | 1/1997 | |
| EP | 1 514 941 | 3/2005 | |
| WO | WO 98/04725 | 2/1998 | |
| WO | WO 98/07834 | 2/1998 | |
| WO | WO 98/36083 | 8/1998 | |
| WO | WO 98/53083 | 11/1998 | |
| WO | WO 99/32619 | 7/1999 | |
| WO | WO 99/53050 | 10/1999 | |
| WO | WO00/078975 | 12/2000 | |
| WO | WO 00/78975 | * 12/2000 | |
| WO | WO 01/09299 | * 2/2001 | |
| WO | WO 01/35725 | 5/2001 | |
| WO | WO 02/15675 | 2/2002 | |
| WO | WO03/000898 | 1/2003 | |
| WO | WO 03/013227 | 2/2003 | |

OTHER PUBLICATIONS

Definition of "against"; http://dictionary.reference.com/browse/against. pp. 1-5.*

Donald et al. Mutation of either G box or I box sequences profoundly affects expression from the *Arabidopsis* rbcS-1A promoter. (1990) The EMBO Journal, vol. 9, pp. 1717-1726.*

Benfey et al. The cauliflower mosaic virus 35S promoter: combinatorial regulation of transcription in plants. (1990) Science, vol. 250, pp. 959-966.*

Kim et al. A 20 nucleotide upstream element is essential for the nopaline synthase (nos) promoter activity. (1994) PMB, vol. 24, pp. 105-117.*

Thomas et al. Size constraints for targeting post-transcriptional gene silencing and for RNA-directed methylation in *Nicotiana benthamiana* using a potato virus X vector. (2001) The Plant Journal, vol. 25, pp. 417-425.*

*Primary Examiner*—Stuart F. Baum
*Assistant Examiner*—Cathy Kingdon Worley
(74) *Attorney, Agent, or Firm*—Fish & Richardson P.C.

(57) ABSTRACT

Rice sucrose synthase 3 regulatory regions suitable for directing expression of a heterologous nucleic acid are described, as well as nucleic acid constructs that include these regulatory regions. Also disclosed are transgenic plants that contain such constructs and methods of producing such transgenic plants.

18 Claims, No Drawings

OTHER PUBLICATIONS

GenBank Accession No. C10692, Aug. 14, 2006.
GenBank Accession No. U53501, May 6, 1996.
GenBank Accession No. Z97335, Nov. 14, 2006.
GenBank Accession No. AC002130, Aug. 16, 2000.
GenBank Accssion No. AC002396, Oct. 30, 2002.
GenBank Accession No. AC002986, May 23, 1998.
GenBank Accession No. AC007067, Jun. 28, 2000.
GenBank Accession No. AF014824, Aug. 12, 1997.
GenBank Accession No. AL021635, Nov. 14, 2006.
GenBank Accession No. AL021711, Nov. 14, 2006.
GenBank Accession No. AL035538, Nov. 14, 2006.
GenBank Accession No. AC093713, May 29, 2003.
GenBank Accession No. AF063403, May 14, 1998.
GenBank Accession No. AF096096, Jan. 25, 1999.
GenBank Accession No. AF129516, Apr. 6, 1999.
GenBank Accession No. AT5G49160, Jul. 22, 2005.
GenBank Accession No. L05934, Oct. 22, 1993.
GenBank Accession No. U39944, Feb. 4, 2003.
GenBank Accession No. U76670, Jan. 23, 1997.
GenBank Accession No. U93215, Feb. 27, 2002.
GenBank Accession No. L10692, Jul. 26, 1993.
GenBank Accession No. AJ002140, Apr. 15, 2005.
GenBank Accession No. AF007807, Feb. 19, 1998.
GenBank Accession No. AF034419, Mar. 2, 1998.
Abler and Scandalios, "Isolation and Characterization of a genomic sequence encoding the maize Cat3 catalase gene," *Plant Mol Biol.*, 1993, 22(6):1031-1038.
Adams et al., "Parent-of-origin effects on seed development in *Arabidopsis thaliana* require DNA methylation," *Development*, 2000, 127:2493-3502.
Alexander and Wulff, "Experimental Ecological Genetics in Plantago: X. The Effects of Maternal Temperature on Seed and Seeding Characters in *P. lanceolata*," *J. Ecology*, 1985, 73(1):271-282.
Altschul et al, "Gapped Blast and PSI-Blast: a new generation of protein database search programs" *Nucl. Acids Res.*, 1997, 25:3389.
Angenent et al., "A Novel Class of MADS Box Genes is Involved in Ovule Development in Petunia," *Plant Cell*, 1995, 7:1569-1582.
Bateman et al, "Pfam 3.1: 1313 multiple alignments and profile HMMs match the majority of proteins," *Nucl. Acids Res.*, 1999, 27:260-262.
Bechtold et al., "*In planta Agrobacterium* mediated gene transfer by infiltration of adult *Arabidopsis thaliana* plants" *C.R. Acad. Sci. Paris*, 1993, 316:1194-1199.
Bender and Fink, "Epigenetic Control of an Endogenous Gene Family Is Revealed by a Novel Blue Fuoroscent Mutant of *Arabidopsis*," *Cell*, 1995, 83:725-734.
Bernacchia et al. "Carrot DNA-methyltransferase is encoded by two classes of genes with differing patterns of expression" *The Plant Journal*,1998, 13(3):317-329.
Bestor and Verdine, "DNA methyltransferases" *Current Opinion in Cell Biology*, 1994, 6:380-389.
Bevan, "Binary *Agrobacterium* vectors for plant transformation," *Nucleic Acids Res.*, 1984, 12(22):8711-8721.
Bhattacharya et al., "A mammalian protein with specific demethylase activity for mCpG DNA," *Nature*,1999, 397:579-583.
Bolitho et al., "Antisense apple ACC-oxidase RNA reduces ethylene production in transgenic tomato fruit" *Plant Science*, 1997, 122:91-99.
Bourque "Antisense strategies for genetic manipulations in plants" *Plant Science*, 1995, 105:125-149.
Bowie et al., "Deciphering the Message in Protein Sequences: Tolerance to Amino Acid Substitutions" *Science*, 1990, 247:1306-1310.
Brink and Cooper, "The Endosperm in Seed Development," *The Botanical Review*, 1947, 13:423-541.
Brown et al. "Development of the endosperm in Rice (*Oryza sativa* L.): Cellularization" *J. Plant Res.*, 109:301-313 (1996.
Brummell et al., "Inverted repeat of a heterologous 3'-untranslated region for high-efficiency, high-throughput gene silencing," *Plant J.*, 2003, 33:793-800.

Brutnell and Dellaporta, "Somatic Inactivation and Reactivation of *Ac* Associated With Changes in Cytosine Methylation and Transposase Expression," *Genetics*, 1994, 138:213-225.
Bushell et al., "The Basis of Natural and Artificial Postzygotic Hybridization Barriers in *Arabidopsis* Species," *The Plant Cell*, 2003, 15: 1430-1442.
Bustos, et al., "Regulation of *B*-Glucuronidase Expression in Transgenic Tabacoo Plants by an A/T-Rich, *cis*,Acting Sequence Found Upstream of a French Bean *B*-Phaseolin Gene," *Plant Cell*, 1989, 1:839-854.
Cannon et al., "Organ-specific modulation of gene expression in transgenic plants using antisense RNA," *Plant Molecular Biology*, 1990, 15:39-47.
Cao et al, "Locus-specific control of asymmetric and CpNpG methylatation by the DRM and CMT3 methyltransferase genes," *PNAS*, Dec. 10, 2002, 99(4):16491-16498.
Carron et al., "Genetic modification of condensed tannin biosynthesis in *Lotus corniculatus*.1. Heterologous antisense dihydroflavonol reductase down-regulates tannin accumulation in "hairy root" cultures" *Theor. Appl. Genet.*, 1994, 87:1006-1015.
Ch'ng et al., "Antisense RNA complementary to 3' coding and noncoding sequences of creatine kinase is a potent inhibitor of translation in vivo," *Proc. Natl. Acad. Sci.* USA, Dec. 1989, 86:10006-10010.
Chaudhuri and Messing, "Allele-specific parental imprinting of *dzrl*, a posttranscriptional regulator of zein accumulation," *Proc. Natl. Acad. Sci.* USA, 1994, 91:4867-4871.
Chaudhury et al., "Fertilization-independent seed development in *Arabidopsis thaliana*," *Proc. Natl. Acad. Sci.* USA, 1997, 94:4223-4228.
Chen et al., "Gene dosage and stochastic effects determine the severity and direction of uniparental ribosomal RNA gene silencing (nucleolar dominance) in *Arabidopsis* allopolyploids," *Proc. Natl. Acad. Sci.* USA, 1998, 95:14891-14896.
Choi et al., "Demeter, a DNA glycosylase domain protein, is required for endosperm gene imprinting nad seed vioability in *Arabidopsis*" *Cell*, 110:33-42 (2002).
Choi et al., "Control of Gene Imprinting in *Arabidopsis*," XVIII International Congress on Sexual Plant Reproduction, Beijing, China, Aug. 20-24, 2004.
Chuang et al., "Specific and heritable genetic interference by double-stranded RNA in *Arabidopsis thaliana*," *Proc. Natl. Acad. Sci.* USA, Apr. 25, 2000, 97(9):4985-4990.
Colliver et al., "Differential modification of flavonoid and isoflavonoid biosynthesis with an antisense chalcone synthase construct in transgenic *Lotus corniculatus*" *PMB*, 35:509-522 (1997).
Colombo et al., "The Petunia MADS Box Gene *FB11* Determines Ovule Identify," *Plant Cell*, 1995, 7:1859-1868.
Conceicao, "A cotyledon regulatory region is responsible for the different spatial expression patterns of *Arabidopsis* 2S albumin genes," *Plant*, 1994, 5:493-505.
de Feyter and Gaudron, Methods in Molecular Biology, vol. 74, Chapter 43, "Expressing Ribozymes in Plants," Edited by Turner, P.C, *Humana Press Inc.*, Totowa, NJ, 1997, Jun. 12, 2008.
Dorlhac de Borne et al., "Co-suppression of nitrate reductase host genes and transgenes in transgenic tobacco plants," *Mol. Gen. Genet.*, 1994, 243:613-621.
Duvick, "Genetic Contributions to Advances in Yield of U.S. Maize," *Maydica*, 1992, 37:69-79.
Ehlenfeldt and Ortiz, "Evidence on the nature and origins of endosperm dosage requirements in *Solanum* and other angiosperm genera," *Sex Plant Reprod.*, 1995, 8:189-196.
Einset "Differential expression of antisense in regenerated tobacco plants transformed with an antisense version of a tomato ACC oxidase gene" *Plant Cell*, 1996, 46:137-141.
Elkind et al. "Abnormal plant development and down-regulation of phenylpropanoid biosynthesis in transgenic tobacco containing a heterologous phenylalanine ammonia-lyase gene" *Proc. Natl. Acad. Sci.* USA, 1990, 87:9057-9061.
Elomaa et al. "Transformation of antisense constructs of the chalcone synthase gene superfamily into *Gerbera hybrida*: differential effect on the expression of family members" *Molecular Breeding*, 2:41-50 (1996).

Emery et al., "Radial patterning of *Arabidopsis* shoots by class III HD-ZIP and KANADI genes" *Current Biology*, 2003, 13:1768-1774.

Faske et al. "Transgenic tobacco plants expressing pea chloroplast Nmdh cDNA in sense and antisense orientation" *Plant Physiol.*, 1997, 115:705-715.

Finnegan et al., "Isolation and identification by sequence homology of a putative cytosine methyltransferase from *Arabidopsis thaliana*," *Nucleic Acids Research*, 1993, 21(10):2383-2388.

Finnegan et al., "Reduced DNA methylation in *Arabidopsis thaliana* results in abnormal plant development," *Proc. Natl. Acad. Sci.* USA, 1996, 93:8449-8454.

Finnegan et al. "DNA Methylation in plants" *Annu. Rev. Plant Physiol. Plant Mol. Biol.*, 1998, 49:223-247.

Flavell et al., "Developmental Regulation of Co-suppression in *Petunia hybrida*," *Current Topics in Microbiology and Immunology*, 1995, 197:43-56.

Foster et al., "A *Brassica napus* mRNA encoding a protein homologous to phospholipid transfer proteins, is expressed specifically in the tapetum and developing microspores," *Plant Science*, 1992, 84:187-192.

Fourgoux-Nicol et al. "Isolation of rapeseed genes expressed early and specifically during development of the male gametophyte" *Plant Molecular Biology*, 1999, 40:857-872.

Fromm et al., "Stable transformation of maize after gene transfer by electroporation," *Nature*, 1986, 319:791-793.

Guatelli et al., "Isothermal, in vitro amplification of nuclic acids by a multienzyme reation modeled after retrovial replication" *Proc. Natl. Acad. Sci.* USA 87:1874-1878 (1990).

Gehring et al., "Imprinting and Seed Development," *The Plant Cell*, 2004, 16:S203-S213.

Giroux et al., "A single gene mutation that increases maize seed weight," *Proc. Natl. Acad. Sci.* USA, 1996, 93:5824-5829.

Goll and Bestor "Eukaryotic cytosine methyltransferases" *Annu. Rev. Biochem.*, 2005, 74:481-514.

Goto and Meyerowitz, "Function and regulation of the *Arabidopsis* floral homeotic gene *PISTILLATA*," *Genes & Development*, 1994, 8:1548-1560.

Green, et al., "Binding site requirements for pea nuclear protein factor GT-1 correlate with sequences required for light-dependent transcriptional activation of the *rbc*S-3A gene," *EMBO J.*, 1988, 7:4035-4044.

Grossniklaus et al., "Maternal Control of Embryogenesis by MEDEA, a *Polycomb* Group Gene in *Arabidopsis*," *Science*, 1998, 280:446-450.

Gruenbaum et al., "Sequences specificity of methylation in higher plant DNA," *Nature*, 1981, 292:860-862.

Guberac et al., "Influence of seed size on germinability, germ length, rootlet length and grain yield in spring oat," *Die Bodenkultur*, 1998, 49(1):13-18.

Gutterson, "Anthocyanin Biosynthetic Genes and Their Application To Flower Color Modification through Sense Suppression" *HortScience*, 1995, 30(5):964-966.

Haig and Westoby, "Genomic imprinting in endosperm: its effect on seed development in crosses between species, and between different ploidies of the same species, and its implications for the evolution of apomixis," *Phil. Trans. R. Soc. Lond. B*, 1991, 333:1-13.

Hamilton et al., "A transgene with repeated DNA causes high frequency, post-transcriptional suppression of ACC-oxidase gene expression in tomato," *The Plant Journal*, 1998, 15(6):737-746.

Hamilton et al., "A Species of Small Antisense RNA in Post-transcriptional Gene Silencing in Plants," *Science*, Oct. 29, 1999, 286(5441):950-952.

Hannah and Greene, "Maize Seed Weight is Dependent on the Amount of Endosperm ADP-glucose Pyrophosphorylase," *J. Plant Physiol.*, 1998, 152:649-652.

Herbik et al., "Isolation, characterization and cDNA cloning of nicotianamine synthase from barley" *Eur. J. Biochem.*, 1999, 265:231-239.

Hibino et al. "Increase of cinnamaldehyde groups in lignin of transgenic tobacco plants carrying an antisense gene for cinnamyl alcohol dehydrogenase" *Biosci. Biotech. Biochm.*, 1995, 59(5):929-931.

Hoe-Huh, et al, "Regulation of Gene Imprinting in *Arabidopsis*," *Seed Development Symposium Sponsored by the Biology Department, University of Saskatchewan*, Canada, May 12-13, 2005.

Irish and Yamamoto, "Conservation of Floral Homeotic Gene Function between *Arabidopsis* and *Antirrhinum*," *Plant Cell*, 1995, 7:1635-1644.

Jack et al., "The Homeotic Gene *APETALA3* of *Arabidopsis thaliana* Encodes a MADS Box and Is Expressed in Petals and Stamens," *Cell*, 1992, 68:683-697.

Jacobsen and Meyerowitz "Hypermethylated Superman epigenetic alleles in *Arabidopsis*" *Science*, 1997, 277:1100-1103.

Jacobsen et al. "Ectopic hypermethylation of flower-specific genes in *Arabidopsis*" *Current Biology*, 2000, 10:179-186.

Jeddeloh et al., "CCG methylation in angiosperms,"0 *Plant J.*, 1996, 9:579-586.

Jones et al., "Methylated DNA and MeCP2 recruit histone deacetylase to repress transcription," *Nature Genetics*, 1998, 19:187-191.

Jordano, et al., "A Sunflower Helianthinin Gene Upstream Sequence Ensemble Contains an Enhancer and Sites of Nuclear Protein Interaction," *Plant Cell*, 1989, 1:855-866.

Jorgensen et al., "Altered gene expression in plants due to *trans* interactions between homologous genes," *TIB*, 8:340-344 (1990).

Jorgensen et al., "Do unintended antisense transcripts contribute to sense cosuppression in plants?," *TIG*, Jan. 1999, 15(1):11-12.

Kakutani et al., "Characterization of an *Arabidopsis thaliana* DNA hypomethylation mutant," *Nucleic Acids Res.*, 1995, 23:130-137.

Kakutani et al., "Development abnormalities and epimutations associated with DNA hypomethylation mutations," *Proc. Natl. Acad. Sci.* USA, 1996, 93:12406-12411.

Kankel et al., "*Arabidopsis* MET1 Cytosine Methyltransferase Mutants," *Genetics*, 2003, 163:1109-1122.

Karlin et al, "Methods for assessing the statistical significance of molecular sequence features by using general scoring schemes," *Proc. Natl. Acad. Sci.*, 1990, 87:2264-2268.

Karlin et al, "Applications and statistics for multiple high-scoring segments in molecular sequences," *Proc. Natl. Acad. Sci.* USA, 1993, 90:5873.

Kass et al., "DNA methylation directs a time-dependent repression of transcription initiation," *Current Biology*, 1997, 7:157-165.

Kermicle and Alleman, "Gametic imprinting in maize in relation to the angiosperm life cycle," *Development*, 1990, Supplement, pp. 9-14.

Kinoshita et al., "Polycomb repression of flowering during early plant development," *Proc. Natl. Acad. Sci.* USA, 2001, 98:14156-14161.

Kishimoto et al., "Site specificity of the *Arabidopsis* MET1 DNA methyltransferase demonstrated through hypermethylation of the superman locus," *Plant Molecular Biology*, 2001, 46:171-183.

Kiyosue et al., "Control of fertilization-independent endosperm development by the *MEDEA* polycomb gene in *Arabidopsis*," *Proc. Natl. Acad. Sci.* USA, 1999, 96:4186-4191.

Koltunow et al., "Apomixis: Molecular Strategies for the Generation of Genetically Identical Seeds without Fertilization," *Plant Physiol.*, 1995, 108:1345-1352.

Krannitz et al., "The Effect of Genetically Based Differences in Seed Size on Seedling Survival in *Arabibopsis thaliana* (Brassicaceae)," *Am. J. Botany*, 1991, 78(3):446-450.

Lan et al., "Monitoring of gene expression profiles and isolation of candidate genes involved in pollination and fertilization in rice (*Oryza sativa* L.) with a 10K cDNA microarray" *Plant Mol. Biol.* 54(4):471-87 (2004).

Laherty et al., "Histone Deacetylases Asssociated with the mSin3 Corepressor Mediate Mad Transcriptional Repression," *Cell*, 1997, 89:349-356.

Lewis, *Genetic Engineering News*, 12(9):1 (1992).

Li et al., "Role for DNA methylation in genomic imprinting," *Nature*, 1993, 366:362-365.

Li et al., "An Argonaute4-containing nuclear processing center colocalized with cajal bodies in *Arabidopsis thaliana*" *Cell*, 126:93-106.

Liu et al., "Multiple Domains are Involved in the Targeting of the Mouse DNA Methyltransferase to the DNA Replication Foci," *Nucleic Acids Research*, 1998, 26(4):1038-1045.

Lindroth et al., "Requirement of Chromomethylase3 for Maintenance of CpXpG Methylation," *Science*, Jun. 15, 2001, 292:2077-2080.

Lund et al., "Endosperm-specific demethylation and activation of specific alleles of α-tubulin genes of *Zea mays* L.," *Mol. Gen. Genet.*, 1995, 246:716-722.

Luo et al., "Genes controlling fertilization-independent seed development in *Arabidopsis thaliana*," *Proc. Natl. Acad. Sci.* USA, 1999, 96:296-301.

Luo et al., "Expression and Parent-of-Origin Effetcs for FIS2, MEA, and FIE in the Endosperm and Embryo of Developing *Arabidopsis* Seeds," *Proc. Natl. Acad. Sci.* USA, 2000, 97(19):10637-10642.

Manga and Yadav, "Effect of seed size on developmental traits and ability to tolerate drought in pearl millet," *J. Arid Environments*, 1995, 29:169-172.

Marshall, "Effect of Seed Size on Seedling Success in Three Species of *Sesbania* (Fabaceae)," *Amer. J. Bot.*, 1986, 73(4):457-464.

Martienssen and Richards, "DNA methylation in eukaryotes," *Curr. Opin. Genet. Dev.*, 1995, 5:234-242.

Mascia et al., "Safe and acceptable strategies for producing foreign molecules in plants," *Current Opinion in Plant Biology*, 2004, 7:189-195.

Matzke and Matzke, "How and Why Do Plants Inactivate Homologous (Trans)genes?" *Plant Physiol.*, 1995, 107:679-685.

Mazzolini et al. "Assaying synthetic ribozymes in plants: high-level expression of a functional hammerhead structure fails to inhibit target gene activity in transiently transformed protoplasts" *Plant Molecular Biology*, 1992, 20:715-731.

McConnell et al. "Role of PHABULOSA and PHAVOLUTA in determining radial patterning in shoots" *Nature*, 2001, 411(6838):709-713.

Meier, et al., "Elicitor-Inducible and Constitutive in Vivo DNA Footprints Indicate Novel *cis*-Acting Elements in the Promoter of a Parsley Gene Encoding Pathogenesis-Related Protein 1," *Plant Cell*, 1991, 3:309-316.

Merlo et al., "Ribozymes Targeted to Stearoyl-ACP Δ9 Desaturase mRNA Produce Heritable Increases of Stearic Acid in Transgenic Maize Leaves," *The Plant Cell*, 1998, 10: 1603-1621.

Myers and Dean "Sensible use of antisense: how to use oligonucleotides as research tools" *TiPS*, Jan. 2000, 21:19-23.

Nakano et al., "A Tobacco NtMET1 cDNA Encoding a DNA Methyltransferase: Molecular Characterization and Abnormal Phenotypes of Transgenic Tobacco Plants," *Plant Cell Physiol.*, 2000, 41(4):448-457.

Nan et al., "Transcriptional repression by the methyl-CpG-binding protein MeCP2 involves a histone deacetylase complex," *Nature*, 1998, 393:386-389.

Napoli et al., "Introduction of a Chimeric Chalcone Synthase Gene into Petunia Results in Reversible Co-Suppression of Homologous Genes in trans," *Plant Cell*, 1990, 2:279-289.

Niebel et al., "Co-suppression of B-1, 3-Glucanase Genes in *Nicotiana tabacum*," *Current Topics in Microbiology and Immunology*, 1995, 197:91-103.

Ohad et al., "A mutation that allows endosperm development without fertilization," *Proc. Natl. Acad. Sci.* USA, 1996, 93:5319-5324.

Ohad et al., "Mutations in FIE, a WD Polycomb Group Gene, Allow Endosperm Development without Fertilization," *The Plant Cell*, 1999, 11:407-415.

Oliver et al. "Inhibition of tobacco NADH-hydroxypyruvate reductase by expression of a heterologous antisense RNA derived from a cucumber cDNA: Implications for the mechanism of action of antisense RNAs" *Mol. Gen. Genet.*, 1993, 239:425-434.

Palauqui et al., "Field trial analysis of nitrate reductase co-suppression: a comparative study of 38 combinations of transgene loci," *Plant Molecular Biology*, 1995, 29:149-159.

Pazin and Kadonaga, "What's Up and Down with Histone Deacetylation and Transcription?" *Cell*, 1997, 89:325-328.

Perriman et al., "Effective ribozyme delivery in plant cells" *Proc. Natl. Acad. Sci.* USA 92(13):6175-6179 (1995).

Ponger and Li "Evolutionary diversification of DNA methyltransferases in eukaryotic genomes" *Molecular Biology and Evolution*, 2005, 22:1119-1128.

Pontes et al. "The *Arabidopsis* chromatin-modifying nuclear siRNA pathway involves a nucleolar RNA processing center" *Cell*, 2006 126:79-92.

Ray, "*Arabidopsis* floral homeotic gene Bell (BEL1) controls ovule development through negative regulation of AGAMOUS gene (AG)," *Proc. Natl. Acad. Sci.* USA, 1994, 91:5761.

Razin, "CpG methylation, chromatin structure and gene silencing—a three-way connection," *EMBO J.*, 1998, 17(17):4905-4908.

Reiser et al., "The *BELL1* Gene Encodes a Homeodomain Protein Involved in Pattern Formation in the *Arabidopsis* Ovule Primordium," *Cell*, 1995, 83:735-742.

Richards, "DNA methylation and plant development," *Trends in Genetics*, 1997, 13(8):319-323.

Roberts et al., "Gametophytic and sporophytic expression of an anther-specific *Arabidopsis thaliana* gene," *Plant J.*, 1993, 3(1):111-120.

Robinson, "Altered gene expression in plants due to trans interactions between homologous genes," *TIBTECH*, Dec. 1990, 8:340-344.

Roeckel et al., "Phenotypic alterations and component analysis of seed yield in transgenic *Brassica napus* plants expressing the *tzs* gene," *Physiologia Plantarum*, 1998, 102:243-249.

Ronemus et al., "Demethylation-Induced Developmental Plieotropy in *Arabidopsis*," *Science*, 1996, 273:654-656.

Salehuzzaman et al. "Isolation and characterization of a cDNA encoding granule-bound starch synthase in cassava (*Manihot esculenta* Crantz) and its antisense expression in potato" *Plant Molecular Biology*, 1993, 23:947-962.

Sambrook et al., Molecular Cloning, A Laboratory Manual, 1989, Sections 9.37-9.52, 2nd Edition, Cold Spring Harbor Press, Plainview; NY.

Savidge et al., "Temporal Relationship between the Transcription of Two *Arabidopsis* MADS Box Genes and the Floral Organ Identity Genes," *The Plant Cell*, Jun. 1995, 7:721-733.

Saze et al, "Maintenance of CpG Methylation is essential for epigenetic inheritance during plant gametogenesis," *Nature Genetics*, May 2003, 34:65-69.

Schaal, "Reproductive Capacity and Seed Size in *Lupinus texensis*," *Amer. J. Bot.*, 1980, 67(5):703-709.

Scott et al., "Parent-of-origin effects on seed development in *Arabidopsis thaliana*," *Development*, 1998, 125:3329-3341.

Sessions et al., "Patterning the floral meristem," *Seminars in Cell & Developmental Biology*, 1998, 9:221-226.

Sharp, "RNAi and double-strand DNA," *Genes & Development*, 1999, 13:139-141.

Sheehy et al., "Reduction of polygalacturonase activity in tomato fruit by antisense RNA," *Proc. Natl. Acad. Sci.* USA, Dec. 1988, 85:8805-8809.

Sheridan, "The *macl* Gene: Controlling the Commitment to the Meiotic Pathway in Maize," *Genetics*, 1996, 142:1009-1020.

Smyth, "Gene silencing: Cosuppression at a distance," *Current Biology*, 1997, 7:R793-R795.

Solter, "Differential Imprinting and Expression of Maternal and Paternal Genomes," *Annu. Rev. Genet.*, 1988, 22:127-146.

Sonnhammer et al, "Pfam: multiple sequence alignments and HMM-profiles of protein domains," *Nucl. Acids Res.*, 1998, 26: 320-322.

Sonnhammer et al, "Pfam: A comprehensive Database of Protein Domain Families Based on Seed Alignments," *Proteins*, 1997, 28:405-420.

Stoskopf et al., "Chapter 17—Interspecific and Intergeneric Hybridization," *Plant Breeding—Theory and Practice*, 1993, Westview Press, Boulder, CO, pp. 345-371.

Taylor, "Comprehending Cosuppression," *The Plant Cell*, Aug. 1997, 9:1245-1249.

Teerawanichpan et al. "Characterization of two rice DNA methyltransferase genes and RNAi-mediated reactiviation of a silenced transgene in rice callus," *Planta*, 2004, 218: 337-349.

Temple et al. "Modulation of glutamine synthetase gene expression in tobacco by the introduction of an alfalfa glutamine synthase gene in sense and antisense orientation: molecular and biochemical analysis" *Mol. Gen. Genet.*, 1993, 236:315-325.

Trevanion et al. "NADP-Malate dehydrogenase in the $C_4$ plant *Flaveria bidentis*" *Plant Physiol.*, 1997, 113:1153-1165.

Tuschl et al., "Targeted mRNA degradation by double-stranded RNA in vitro," *Genes & Development*, 1999, 13:3191-3197.

Urao, "Molecular cloning and characterization of a gene that encodes a MYC-related protein in *Arabidopsis*," *Plant Mol. Biol.*, 1996, 32:571-557.

Van der Krol et al, "Modulation of Eukaryotic Gene Expression by Complementary RNA or DNA Sequences," *BioTechniques*, 1988, 6(10):958-976.

Van der Krol et al. "An anti-sense chalcone synthase gene in transgenic plants inhibits flower pigmentation" *Nature*, 1988, 333:866-869.

Vaucheret et al., "Molecular and genetic analysis of nitrite reductase co-suppression in transgenic tobacco plants," *Mol. Gen. Genet.*, 1995, 248:311-317.

Veena et al. "Glyoxalase I from *Brassica juncea*: molecular cloning, regulation and its over-expression confer tolerance in transgenic tobacco under stress" *The Plant Journal*, 1999, 17(4):385-395.

Vinkenoog et al., "Hypomethylation Promotes Autonomous Endosperm Development and rescues Postfertilization Lethality in fie Mutants," *The Plant Cell*, 2000, 12:2271-2282.

Visser et al. "Inhibition of the expression of the gene for granule-bound starch synthase in potato by antisense constructs" *Mol. Gen. Genet.*, 1991, 225:289-296.

Voinnet et al., "Suppression of gene silencing: A general strategy used by diverse DNA and RNA viruses of plants," *Proc. Natl. Acad. Sci.* USA, Nov. 23, 1999, 96(24):14147-14152.

Vongs et al., "*Arabidopsis thaliana* DNA Methylation Mutants," *Science*, 1993, 260:1926-1928.

Wada et al., "Association between up-regulation of stress-responsive genes and hypomethylation of genomic DNA in tobacco plants," *Mol. Gen. Genomics*, 2004, 271:658-666.

Waterhouse et al., "Virus resistance and gene silencing in plants can be induced by simultaneous expression of sense and antisense RNA," *Proc. Natl. Acad. Sci.* USA, 1998, 95:13959-13964.

Weiss, "Hot prospect for new gene amplifier" *Science*, 254:1292 (1991).

Winn, "Effects of Seed Size and Microsite on Seedling Emergence of *Prunella Vulgaris* in Four Habitats," *J. Ecology*, 1985, 73:831-840.

Wulff, "Seed Size Variation in *Desmodium paniculatum*," *J. Ecology*, 1986, 74:99-114.

Xiao et al, "Imprinting of the *MEA* Polycomb Gene Is Controlled by Antagonism between MET1 Methyltransferase and DME Glycosylase," *Development Cell*, 2003, 5:891-901.

Yadegari et al., "Mutations in the FIE and MEA Genes that Encode Interacting Polycomb Proteins Cause Parent-of-Origin Effect on Seed Development by Distinct Mechanisms," *The Plant Cell*, 2000, 12:2367-2381.

Yang et al. "Correlation of cytokinin levels in the endosperms and roots with cell number and cell division activity during endosperm development in rice" *Annals. Of Botany*, 90:369-377 (2002).

Yang et al., "Ribozyme-mediated high resistance against potato spindle tuber viroid in transgenic potatoes," *Proc. Natl. Acad. Sci.* USA, 1997, 94: 4861-4865.

Zhang, et al., "DNA Sequences That Activate Isocitrate Lyase Gene Expression during Late Embryogenesis and during Postgerminative Growth," *Plant Physio.*, 1996, 110:1069-1079.

\* cited by examiner

SUCROSE SYNTHASE 3 PROMOTER FROM RICE AND USES THEREOF

CROSS-REFERENCE TO RELATED APPLICATIONS

This application is a continuation-in-part of, and claims the benefit of and priority under 35 U.S.C. § 120 to U.S. patent application Ser. No. 10/966,482, filed Oct. 14, 2004, which is incorporated by reference in its entirety herein.

TECHNICAL FIELD

This document provides compositions and methods involved in regulating gene expression in eukaryotic organisms (e.g., plants).

BACKGROUND

An essential element for genetic engineering of plants is the ability to express genes using various regulatory regions. The expression pattern of a transgene, conferred by a regulatory region is critical for the timing, location, and conditions under which a transgene is expressed, as well as the intensity with which the transgene is expressed in a transgenic plant. There is continuing need for suitable regulatory regions that can facilitate transcription of sequences that are operably linked to the regulatory region

SUMMARY

This document provides compositions and methods involving regulatory regions having the ability to direct transcription in eukaryotic organisms (e.g., plants). For example, this document provides regulatory regions having the ability to direct transcription in plant ovules prior to fertilization and in seeds during early stages of development. Also provided herein are nucleic acid constructs, plant cells, and plants containing such regulatory regions; methods of producing plant cells and plants containing such regulatory regions; and methods of using such regulatory regions to express polynucleotides in plants and to alter the phenotype of plant cells. Regulatory regions that direct transcription during seed development can be used, for example, to manipulate genomic imprinting in crop plants, resulting in enhanced seed development and increased yield.

In one embodiment, an isolated nucleic acid including a regulatory region having a length of 1735 to 1890 nucleotides and 80 percent or greater sequence identity to SEQ ID NO:1 is provided, where the regulatory region directs transcription, in a plant ovule within 24 hours post-fertilization, of an operably linked heterologous polynucleotide. The sequence identity can be 85 percent or greater, 90 percent or greater, or 95 percent or greater.

In another embodiment, an isolated nucleic acid including a regulatory region having a nucleic acid sequence corresponding to SEQ ID NO:1 is provided, where the regulatory region directs transcription, in a plant ovule within 24 hours post-fertilization, of an operably linked polynucleotide.

In another embodiment, an isolated nucleic acid including a regulatory region having a length of 1735 to 1890 nucleotides and 80 percent or greater sequence identity to SEQ ID NO:1 is provided, where the regulatory region directs transcription in an unfertilized plant ovule of an operably linked heterologous polynucleotide. The sequence identity can be 85 percent or greater, 90 percent or greater, or 95 percent or greater.

In a further embodiment, an isolated nucleic acid including a regulatory region having a nucleic acid sequence corresponding to SEQ ID NO:1 is provided, where the regulatory region directs transcription in an unfertilized plant ovule of an operably linked polynucleotide.

A regulatory region can include an intron. A regulatory region can include one or more of a TATA box, a CAAT box, a GCN4 box, an endosperm box, a prolamin box, and a legumin box. A regulatory region can include all of a TATA box, a CAAT box, a GCN4 box, an endosperm box, a prolamin box, and a legumin box.

In another aspect, a nucleic acid construct including an isolated nucleic acid including a regulatory region is provided, where the nucleic acid is operably linked to a heterologous polynucleotide. The heterologous polynucleotide can include a nucleic acid sequence encoding a polypeptide. The heterologous polynucleotide can be in an antisense orientation relative to the regulatory region. The heterologous polynucleotide can be transcribed into an antisense RNA capable of inhibiting expression of a DNA methyltransferase. The heterologous polynucleotide can be transcribed into an interfering RNA. The heterologous polynucleotide can be transcribed into an interfering RNA against a DNA methyltransferase.

In another embodiment, a transgenic plant or plant cell is provided, where the plant or plant cell includes an isolated nucleic acid including a regulatory region operably linked to a heterologous polynucleotide. The plant or plant cell can be a monocot. The heterologous polynucleotide can include a nucleic acid sequence encoding a polypeptide. The heterologous polynucleotide can be in an antisense orientation relative to the regulatory region. The heterologous polynucleotide can be transcribed into an interfering RNA.

In a further embodiment, a seed from a transgenic plant is provided.

In another aspect, a method of producing a transgenic plant is provided. The method can include (a) introducing into a plant cell an isolated polynucleotide including an isolated nucleic acid including a regulatory region operably linked to a heterologous polynucleotide, and (b) growing a plant from the plant cell. The plant can be a monocot. The heterologous polynucleotide can include a nucleic acid sequence encoding a polypeptide. The heterologous polynucleotide can be in an antisense orientation relative to the regulatory region. The heterologous polynucleotide can be transcribed into an interfering RNA.

In another aspect, a transgenic plant produced by the method described above is provided.

In yet another aspect, a seed from a transgenic plant described above is provided.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying description below. Other features, objects, and advantages of the invention will be apparent from the description and from the claims.

DETAILED DESCRIPTION

This document provides isolated nucleic acids comprising regulatory regions. The terms "nucleic acid" and "polynucleotide" are used interchangeably herein, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by the polymerase chain reaction (PCR) or restriction endonuclease treatment) independent of other sequences. An isolated nucleic acid also refers to a DNA molecule that is incorporated into a vector, an autonomously replicating plasmid, a virus, a bacterium, or into the genome of a prokaryote or eukaryote. In addition, an isolated nucleic acid can include an engineered nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Regulatory Regions

A regulatory region described herein is a nucleic acid that can direct transcription of a heterologous nucleic acid in certain cell types when the regulatory region is operably linked 5' to the heterologous nucleic acid. As used herein, "heterologous nucleic acid" refers to a nucleic acid other than the naturally occurring coding sequence to which the regulatory region was operably linked in a plant. With regard to one regulatory region provided herein, pOs530c10 (SEQ ID NO:1), a heterologous nucleic acid is a nucleic acid other than the sucrose synthase 3 coding sequence. The term "operably linked" refers to positioning of a regulatory region and a transcribable sequence in a nucleic acid so as to allow or facilitate transcription of the transcribable sequence. For example, a regulatory region is operably linked to a coding sequence when RNA polymerase is able to transcribe the coding sequence into mRNA, which then can be translated into a protein encoded by the coding sequence.

Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences.

For example, a plant regulatory region can include one or more of the following elements: a CAAT box, a TATA box, a GCN4 box, an endosperm box, a prolamin box, and a legumin box.

The CAAT box is a conserved nucleotide sequence involved in initiation of transcription. The CAAT box functions as a recognition and binding site for regulatory proteins called transcription factors.

The TATA box is another conserved nucleotide sequence involved in transcription initiation. The TATA box seems to be important in determining accurately the position at which transcription is initiated.

The GCN4 box, the endosperm box, and the prolamin box are three different nucleotide sequence motifs that are conserved in the regulatory regions of storage protein genes. These nucleotide sequences are thought to confer endosperm-specific gene expression.

The legumin box, also referred to as the RY repeat motif or the Sph element, is another nucleotide sequence element involved in seed-specific gene expression. The legumin box acts as both an enhancer for seed-specific gene expression and a repressor of expression in vegetative tissue.

The nucleic acid sequence set forth in FIG. 1 and SEQ ID NO:1 is an example of a regulatory region provided herein. However, a regulatory region can have a nucleotide sequence that deviates from that set forth in SEQ ID NO:1, while retaining the ability to direct expression of an operably linked nucleic acid. For example, a regulatory region having 80% or greater (e.g., 81% or greater, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater) sequence identity to the nucleotide sequence set forth in SEQ ID NO:1 can direct expression of an operably linked nucleic acid. The nucleic acid sequences set forth in SEQ ID NOs:2-4 are additional examples of regulatory regions provided herein.

The term "percent sequence identity" refers to the degree of identity between any given query sequence, e.g., SEQ ID NO:1, and a subject sequence. A percent identity for any subject nucleic acid relative to a query nucleic acid can be determined as follows. A query nucleic acid sequence is aligned to one or more subject nucleic acid sequences using the computer program ClustalW (version 1.83, default parameters), which allows alignments of nucleic acid sequences to be carried out across their entire length (global alignment). ClustalW calculates the best match between a query and one or more subject sequences, and aligns them so that identities, similarities, and differences can be determined. Gaps of one or more residues can be inserted into a query sequence, a subject sequence, or both, to maximize sequence alignments. For fast pairwise alignment of nucleic acid sequences, the following parameters are used: word size: 2; window size: 4; scoring method: percentage; number of top diagonals: 4; and gap penalty: 5. For alignment of multiple nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; and gap penalty: 3. For multiple alignment of protein sequences, the following parameters are used: weight matrix: blosum; gap opening penalty: 10.0; gap extension penalty: 0.05; hydrophilic gaps: on; hydrophilic residues: G, P, S, N, D, Q, E, R, K; and residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site (ebi.ac.uk/clustalw).

To determine a percent identity between a query sequence and a subject sequence, ClustalW divides the number of matching nucleotides by the number of nucleotides of the shorter sequence, and multiplies the result by 100. The output is the percent identity of the subject sequence with respect to the query sequence. For example, if a query sequence and a subject sequence are each 500 bases long and have 200 contiguous bases that are identical, the subject sequence would have 40 percent sequence identity to the query sequence. If the two compared sequences are of different lengths, the number of matches is divided by the shorter of the two sequence lengths. For example, if 100 bases match between a 400 nucleotide query sequence and a 500 nucleotide subject sequence, the subject sequence would have 25 percent identity to the query sequence. If the shorter sequence is less than 150 bases in length, the number of matches are divided by 150 and multiplied by 100 to obtain a percent sequence identity.

It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2. It is also noted that the length value will always be an integer.

A regulatory region featured herein can be made by cloning 5' flanking sequences of a sucrose synthase 3 gene, as described in more detail below. Alternatively, a regulatory region can be made by chemical synthesis and/or polymerase chain reaction (PCR) technology. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in PCR Primer: *A Laboratory Manual*, Ed. by Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplification. See, for example, Lewis, *Genetic Engineering News* 12(9):1 (1992); Guatelli et al., *Proc. Natl. Acad. Sci. USA* 87:1874-1878 (1990); and Weiss, *Science* 254:1292 (1991). Various PCR strategies also are available by which site-specific nucleotide sequence modifications can be introduced into a template nucleic acid.

Various lengths of a regulatory region described herein can be made by similar techniques. For example, a regulatory region can be made that has a length of 1735 nucleotides to 1890 nucleotides or any length therebetween, such as a length of 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, or 1889 nucleotides.

The ability of a regulatory region to direct expression of an operably linked nucleic acid can be assayed using methods known to one having ordinary skill in the art. In particular, regulatory regions of varying lengths can be operably linked to a reporter nucleic acid and used to transiently or stably transform a cell, e.g., a plant cell. Suitable reporter nucleic acids include β-glucuronidase (GUS), green fluorescent protein (GFP), yellow fluorescent protein (YFP), and luciferase (LUC). Expression of the gene product encoded by the reporter nucleic acid can be monitored in such transformed cells using standard techniques.

A regulatory region can influence the tissue-specificity of the transcription of an operably linked heterologous nucleic acid. When a heterologous nucleic acid is operably linked to a tissue-, organ-, or cell-specific regulatory region, transcription occurs only or predominantly in a particular tissue, organ, and cell type, respectively. For example, a regulatory region can be essentially specific to a plant ovule. An ovule is a structure in a flower that contains the female gametophyte and develops into a seed. A female gametophyte is also referred to in angiosperms as the embryo sac. The seed is a mature ovule, including the embryo, the endosperm, and the seed coat.

In some cases, a regulatory region can direct transcription primarily in a plant ovule that has not been fertilized, such as in an un-pollinated embryo sac. In some cases, a regulatory region can direct transcription in a plant ovule that has been fertilized, such as in a plant ovule starting within 24 hours post-fertilization to at least five days (e.g., six, seven, eight, nine, 10, 11, 12, 13, or 14 days) after pollination. In some cases, a regulatory region can direct transcription in endosperm tissue starting within 24 hours after fertilization to at least five days after pollination.

Nucleic Acid Constructs

Nucleic acid constructs containing nucleic acids such as those described herein are also provided. A nucleic acid construct can be a vector. A vector is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning, transformation, and expression vectors, as well as viral vectors and integrating vectors. An expression vector is a vector that includes one or more regulatory regions. Suitable expression vectors include, without limitation, plasmids and viral vectors derived from, for example, bacteriophage, baculoviruses, tobacco mosaic virus, herpesviruses, cytomegalovirus, vaccinia viruses, adenoviruses, adeno-associated viruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

A nucleic acid construct includes a regulatory region as disclosed herein. A construct can also include a heterologous nucleic acid operably linked to the regulatory region, in which case the construct can be introduced into an organism and used to direct expression of the operably linked nucleic acid. The heterologous nucleic acid can be operably linked to the regulatory region in the sense or antisense orientation. The regulatory region can be operably linked from approximately 1 to 150 nucleotides upstream of the ATG translation start codon of a heterologous nucleic acid in the sense orientation. For example, the regulatory region can be operably linked 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 25 nucleotides, 30 nucleotides, 35 nucleotides, 40 nucleotides, 45 nucleotides, 50 nucleotides, 55 nucleotides, 60 nucleotides, 65 nucleotides, 70 nucleotides, 75 nucleotides, 80 nucleotides, 85 nucleotides, 90 nucleotides, 95 nucleotides, 100 nucleotides, 110 nucleotides, 120 nucleotides, 130 nucleotides, 140 nucleotides, or 150 nucleotides upstream of the ATG translation start codon of a heterologous nucleic acid in the sense orientation. In some cases, the regulatory region can be operably linked from approximately 151 to 500 nucleotides upstream of the ATG translation start codon of a heterologous nucleic acid in the sense orientation. In some cases, the regulatory region can be operably linked from approximately 501 to 1125 nucleotides upstream of the ATG translation start codon of a heterologous nucleic acid in the sense orientation.

In some embodiments, a heterologous nucleic acid is transcribed and translated into a polypeptide. Suitable polypeptides include, without limitation, screenable and selectable markers such as green fluorescent protein, yellow fluorescent protein, luciferase, β-glucuronidase, or neomycin phosphotransferase II. Suitable polypeptides also include polypeptides that affect growth and/or hormone production. In some embodiments a heterologous nucleic acid encodes a polypeptide involved in nutrient utilization. In other embodiments, a heterologous polynucleotide encodes a non-plant protein of pharmaceutical or industrial interest. In some cases, a heterologous nucleic acid encodes a polypeptide involved in DNA methylation, such as a cytosine DNA methyltransferase.

A nucleic acid construct may include a heterologous nucleic acid that is transcribed into an RNA useful for inhibiting expression of an endogenous gene. Suitable constructs from which such an RNA can be transcribed include antisense constructs. Antisense nucleic acid constructs can include a regulatory region of the invention operably linked, in antisense orientation, to a nucleic acid molecule that is heterologous to the regulatory element. Thus, for example, a transcription product can be similar or identical to the sense coding sequence of an endogenous polypeptide, but transcribed into an RNA that is unpolyadenylated, lacks a 5' cap structure, or contains an unsplicable intron. Constructs containing operably linked nucleic acid molecules in sense orientation can be used to inhibit the expression of a gene. Methods of co-suppression using a full-length cDNA sequence as well as a partial cDNA sequence are known in the art. See, e.g., U.S. Pat. No. 5,231,020.

Alternatively, a heterologous nucleic acid can be transcribed into a ribozyme. See, U.S. Pat. No. 6,423,885. Heterologous nucleic acid molecules can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678. Hammerhead ribozyme sequences can be embedded in a stable RNA such as a transfer RNA (tRNA) to increase cleavage efficiency in vivo. Perriman et al., *Proc. Natl. Acad. Sci. USA* 92(13):6175-6179 (1995); de Feyter and Gaudron, *Methods in Molecular Biology*, Vol. 74, Chapter 43, "Expressing Ribozymes in Plants," Edited by Turner, P.C, Humana Press Inc., Totowa, N.J. RNA endoribonucleases such as the one that occurs naturally in *Tetrahymena thermophila*, and which have been described extensively by Cech and collaborators can be useful. See, for example, U.S. Pat. No. 4,987,071.

A nucleic acid construct also may include a heterologous nucleic acid that is transcribed into an interfering RNA. See, e.g., U.S. Pat. No. 6,753,139; U.S. Patent Publication 20040053876; and U.S. Patent Publication 20030175783. Methods for designing and preparing interfering RNAs to target an endogenous gene are known to those of skill in the art.

An RNA useful for inhibiting expression of an endogenous gene can be one that can anneal to itself, e.g., a double stranded RNA having a stem-loop structure. One strand of the stem portion of a double stranded RNA can comprise a sequence that is similar or identical to the sense coding sequence of an endogenous polypeptide, and that is from about 10 nucleotides to about 2,500 nucleotides in length. In some embodiments, the stem portion is similar or identical to UTR sequences 5' of the coding sequence. In some embodiments, the stem portion is similar or identical to UTR sequences 3' of the coding sequence. The length of the sequence that is similar or identical to the sense coding sequence, the 5' UTR, or the 3' UTR can be from 10 nucleotides to 50 nucleotides, from 10 nucleotides to 500 nucleotides, from 15 nucleotides to 300 nucleotides, from 20 nucleotides to 100 nucleotides, or from 25 nucleotides to 100 nucleotides. In some embodiments the length of the sequence that is similar or identical to the sense coding sequence, the 5' UTR, or the 3' UTR can be from 25 nucleotides to 500 nucleotides, from 25 nucleotides to 300 nucleotides, from 25 nucleotides to 1,000 nucleotides, from 100 nucleotides to 2,000 nucleotides, from 300 nucleotides to 2,500 nucleotides, from 200 nucleotides to 500 nucleotides, from 1,000 nucleotides to 2,500 nucleotides, or from 200 nucleotides to 1,000 nucleotides. The other strand of the stem portion of a double stranded RNA can comprise an antisense sequence of an endogenous polypeptide, and can have a length that is shorter, the same as, or longer than the length of the corresponding sense sequence. The loop portion of a double stranded RNA can be from 10 nucleotides to 2,500 nucleotides in length, e.g., from 15 nucleotides to 100 nucleotides, from 20 nucleotides to 300 nucleotides, from 25 nucleotides to 400 nucleotides, or from 30 to 2,000 nucleotides in length. The loop portion of the RNA can include an intron. See, e.g., WO 98/53083; WO 99/32619; WO 98/36083; WO 99/53050; and U.S. patent publications 20040214330 and 20030180945. See also, U.S. Pat. Nos. 5,034,323; 6,452,067; 6,777,588; 6,573,099; and U.S. Pat. No. 6,326,527.

A suitable interfering RNA also can be constructed as described in Brummell et al., *Plant J.* 33:793-800 (2003).

If desired, a nucleic acid construct further can include a 3' untranslated region (3' UTR), which can increase stability of a transcribed sequence by providing for the addition of multiple adenylate ribonucleotides at the 3' end of the transcribed mRNA sequence. A 3' UTR can be, for example, the nopaline synthase (NOS) 3' UTR. A nucleic acid construct also can contain inducible elements, intron sequences, enhancer sequences, insulator sequences, or targeting sequences other than those present in a regulatory region described herein. Regulatory regions and other nucleic acids can be incorporated into a nucleic acid construct using methods known in the art.

A nucleic acid construct may contain more than one regulatory region. In some embodiments, each regulatory region is operably linked to a heterologous nucleic acid. For example, a nucleic acid construct may contain two regulatory regions, each operably linked to a different heterologous nucleic acid. The two regulatory regions can be the same or different, and one or both of the regulatory regions in such a construct can be a regulatory region described herein.

Transgenic Plants and Cells

The vectors provided herein can be used to transform plant cells and generate transgenic plants. Thus, transgenic plants and plant cells containing the nucleic acids described herein also are provided, as are methods for making such transgenic plants and plant cells. A plant or plant cell can be transformed by having the construct integrated into its genome, i.e., can be stably transformed. Stably transformed cells typically retain the introduced nucleic acid sequence with each cell division. Alternatively, the plant or plant cell also can be transiently transformed such that the construct is not integrated into its genome. Transiently transformed cells typically lose some or all of the introduced nucleic acid construct with each cell division, such that the introduced nucleic acid cannot be detected in daughter cells after sufficient number of cell divisions. Both transiently transformed and stably transformed transgenic plants and plant cells can be useful in the methods described herein.

Typically, transgenic plant cells used in the methods described herein constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

As used herein, a transgenic plant also refers to progeny of an initial transgenic plant. Progeny includes descendants of a particular plant or plant line. Progeny of an instant plant include seeds formed on F1, F2, F3, F4, F5, F6 and subsequent generation plants, or seeds formed on BC1, BC2, BC3, and subsequent generation plants, or seeds formed on FLBC1, F1BC2, F1BC3, and subsequent generation plants. Seeds produced by a transgenic plant can be grown and then selfed (or outcrossed and selfed) to obtain plants and seeds homozygous for the nucleic acid construct.

Alternatively, transgenic plant cells can be grown in suspension culture, or tissue or organ culture. Solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be Murashige and Skoog (MS) medium containing agar and a suitable concentration of an auxin, e.g., 2,4-dichlorophenoxyacetic acid (2,4-D), and a suitable concentration of a cytokinin, e.g., kinetin.

Techniques for transforming a wide variety of higher plant species are known in the art. The polynucleotides and/or recombinant vectors described herein can be introduced into the genome of a plant host using any of a number of known methods, including electroporation, microinjection, and biolistic methods. Alternatively, polynucleotides or vectors can be combined with suitable T-DNA flanking regions and introduced into a conventional *Agrobacterium tumefaciens* host vector. Such *Agrobacterium tumefaciens*-mediated transformation techniques, including disarming and use of binary vectors, are well known in the art. Other gene transfer and transformation techniques include protoplast transformation through calcium or PEG, electroporation-mediated uptake of naked DNA, electroporation of plant tissues, viral vector-mediated transformation, and microprojectile bombardment (see, e.g., U.S. Pat. Nos. 5,538,880; 5,204,253; 5,591,616; and 6,329,571). If a cell or tissue culture is used as the recipient tissue for transformation, plants can be regenerated from transformed cultures using techniques known to those skilled in the art.

The polynucleotides and vectors described herein can be used to transform a number of monocotyledonous plants and plant cell systems, including monocots such as banana, barley, date palm, field corn, garlic, millet, oat, oil palm, onion, pineapple, popcorn, rice, rye, sorghum, sudangrass, sugarcane, sweet corn, switchgrass, turf grasses, and wheat.

Thus, the methods and compositions described herein can be utilized with monocotyledonous plants such as those belonging to the orders *Alismatales, Arales, Arecales, Bromeliales, Commelinales, Cyclanthales, Cyperales, Eriocaulales, Hydrocharitales, Juncales, Liliales, Najadales, Orchidales, Pandanales, Poales, Restionales, Triuridales, Typhales*, and *Zingiberales*.

The methods and compositions can be used over a broad range of plant species, including species from the monocot genera *Agrostis, Allium, Ananas, Andropogon, Asparagus, Avena, Cynodon, Elaeis, Eragrostis, Festuca, Festulolium, Heterocallis, Hordeum, Lemna, Lolium, Musa, Oryza, Panicum, Pennisetum, Phleum, Phoenix, Poa, Saccharum, Secale, Sorghum, Triticum, Zoysia* and *Zea*.

A transformed cell, callus, tissue, or plant can be identified and isolated by selecting or screening the engineered plant material for particular traits or activities, e.g., those encoded by marker genes or antibiotic resistance genes. Such screening and selection methodologies are well known to those having ordinary skill in the art. In addition, physical and biochemical methods can be used to identify transformants. These include Southern analysis or PCR amplification for detection of a polynucleotide; Northern blots, S1 RNase protection, primer-extension, quantitative real-time PCR, or reverse transcriptase PCR (RT-PCR) amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are well known. After a polynucleotide is stably incorporated into a transgenic plant, it can be introduced into other plants using, for example, standard breeding techniques.

A regulatory region disclosed herein can be used to express any of a number of heterologous nucleic acids of interest in a plant. For example, a regulatory region disclosed herein can be used to express a polypeptide or an interfering RNA. In some cases, a regulatory region disclosed herein can be used to express a cytosine DNA methyltransferase in female gametophyte cells of a plant. In some cases, a regulatory region disclosed herein can be used to express an interfering RNA that inhibits transcription of an endogenous cytosine DNA methyltransferase in female gametophyte cells of a plant. Expression of such a polypeptide or interfering RNA can affect the phenotype of a plant (e.g., a transgenic plant) when expressed in the plant, e.g., at the appropriate time(s), in the appropriate tissue(s), or at the appropriate expression levels. Thus, transgenic plants (or plant cells) can have an altered phenotype as compared to a corresponding control plant (or plant cell) that either lacks the transgene or does not express the transgene. A corresponding control plant can be a corresponding wild-type plant, a corresponding plant that is not transgenic but otherwise is of the same genetic background as the transgenic plant of interest, or a corresponding plant of the same genetic background in which expression of the transgene is suppressed, inhibited, or not induced (e.g., where expression is under the control of an inducible promoter). A plant can be said "not to express" a transgene when the plant exhibits less than 10% (e.g., less than 9%, 8%, 7%, 6%, 5%, 4%, 3%, 2%, 1%, 0.5%, 0.1%, 0.01%, or 0.001%) of the amount of the polypeptide, mRNA encoding the polypeptide, or transcript of the transgene exhibited by the plant of interest. Expression can be evaluated using methods including, for example, quantitative real-time PCR, RT-PCR, Northern blots, S1 RNase protection, primer extensions, Western blots, protein gel electrophoresis, immunoprecipitation, enzyme-linked immunoassays, microarray technology, and mass spectrometry. It should be noted that if a transgene is expressed under the control of a tissue-specific or broadly expressing promoter, expression can be evaluated in a selected tissue or in the entire plant. Similarly, if a transgene is expressed at a particular time, e.g., at a particular time during development or upon induction, expression can be evaluated selectively during a desired time period.

Use of a regulatory region provided herein to inhibit transcription of an endogenous cytosine DNA methyltransferase in female gametophyte cells of a plant can, after pollination, lead to the formation of seeds having an increased weight compared to the weight of seeds from a corresponding control plant. In some embodiments, use of the methods and compositions described herein to express a cytosine DNA methyltransferase in female gametophyte cells of a plant can, after pollination, lead to the formation of seeds having a decreased weight compared to the weight of seeds from a corresponding control plant.

Seeds of transgenic plants describe herein can be conditioned and bagged in packaging material by means known in the art to form an article of manufacture. Packaging material such as paper and cloth are well known in the art. Such a bag of seed preferably has a package label accompanying the bag, e.g., a tag or label secured to the packaging material, a label printed on the packaging material, or a label inserted within the bag. The package label may indicate the seed contained therein incorporates transgenes that provide increased seed weight.

The invention will be further described in the following examples, which do not limit the scope of the invention described in the claims.

EXAMPLES

Example 1

Isolation of a 5'-Flanking Region of a Sucrose Synthase Gene

Rice gene expression profiles (Lan et al., *Plant Mol. Biol.* 54(4):471-87 (2004)) were analyzed to identify genes that were highly expressed in pistil five days after pollination and that were not expressed in un-pollinated pistil. Sucrose synthase 3 was identified as such a gene. The expression level of sucrose synthase 3 in pistil five days after pollination was about 28-fold higher than the expression level of sucrose synthase 3 in unpollinated pistil.

The sequence of the sucrose synthase 3 expressed sequence tag (EST) used by Lan et al. to construct a cDNA microarray was retrieved from the website of the National Center for Gene Research, Chinese Academy of Sciences (ncgr.ac.cn/EST.html). The sucrose synthase 3 EST sequence was then compared to sequences in the National Center for Biotechnology Information (NCBI) database using the Basic Local Alignment Search Tool (BLAST), and a corresponding complementary DNA (cDNA) sequence was identified. The cDNA sequence was then compared to cDNA clones in the database of full-length cDNA clones from japonica rice (Knowledge-based Oryza Molecular biological Encyclopedia: KOME; cdna01.dna.affrc.gojp/cDNA/) to identify a predicted full-length cDNA sequence. The predicted full-length cDNA sequence was used to perform a BLAST search and retrieve the corresponding genomic DNA sequence. By aligning the genomic DNA sequence with the coding sequence, the ATG start codon and the 5'-flanking region were identified. Approximately two kilobases of the 5'-flanking region were isolated. This sequence, designated pOs530c10 (SEQ ID NO:1), was cloned into an expression vector such that it was operably linked to a Histone-Yellow Fluorescent Protein (YFP) expression cassette that had previously been tested using a 35S promoter.

Example 2

Analysis of pOs530c10 Activity

Rice of the Kitaake cultivar was transformed with an expression vector containing a Histone-YFP coding sequence under the transcriptional control of pOs530c10. Ten putative transformants were selected and screened for the presence of the transgene using the polymerase chain reaction (PCR) with gene specific primers. The transgene was present in all ten transformants.

Whole ovules were collected from four of the transgenic plants. Approximately ten pre-fertilization ovules were dissected from the pistil of each plant, flash frozen in liquid nitrogen, and pooled for RNA extraction. Post-fertilization ovules were collected separately and processed in a similar manner. RNA samples were extracted from pre- and post-fertilization ovules and analyzed using reverse transcription PCR (RT-PCR). Plants in which expression of the Histone-YFP fusion protein was detected by RT-PCR were analyzed further using confocal microscopy. At least four ovules were dissected from each plant that was positive for Histone-YFP expression according to the RT-PCR assay. Isolated post-fertilization (one to two days after pollination) and pre-fertilization ovules were analyzed for Histone-YFP expression using confocal microscopy with different light channels. Ovules were examined using a YFP channel, a chlorophyll channel, and a bright field.

Microscopy analysis indicated that pOs530c10 was active as a promoter in early stages of seed development. YFP expression was observed in five out of five transformed plants analyzed. YFP expression was observed in seeds as early as 24 hours after pollination. These results suggest that pOs530c10 is active as a promoter in early stages of endosperm development, about one to two days after pollination. In addition, results from other experiments indicated that pOs530c10 was active as a promoter in endosperm at 14 days after pollination.

It has been reported that a promoter may be transcriptionally active at least 24 hours before fluorescence from an operably linked Green Fluorescent Protein (GFP) reporter polypeptide can be visualized. Based on the microscopy data using YFP, pOs530c10 is active immediately after fertilization.

Pre-fertilization ovules arising from plants transformed with the expression vector containing the Histone-YFP coding sequence under the transcriptional control of pOs530c10 were also analyzed. Microscopy analysis carried out as described above indicated that YFP expression also occurred in the embryo sac prior to pollination.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid comprising a regulatory region comprising the nucleotide sequence set forth in SEQ ID NO:1, wherein said regulatory region directs transcription, in a plant ovule within 24 hours post-fertilization, of an operably linked heterologous polynucleotide.

2. The nucleic acid of claim 1 wherein said regulatory region comprises an intron.

3. An isolated nucleic acid comprising a regulatory region comprising the nucleotide sequence set forth in SEQ ID NO:1, wherein said regulatory region directs transcription in an unfertilized plant ovule of an operably linked heterologous polynucleotide.

4. The nucleic acid of claim 3 wherein said regulatory region comprises an intron.

5. A nucleic acid construct comprising the nucleic acid of claim 1 operably linked to a heterologous polynucleotide.

6. The nucleic acid construct of claim 5 wherein said heterologous polynucleotide comprises a nucleic acid sequence encoding a polypeptide.

7. The nucleic acid construct of claim 5 wherein said heterologous polynucleotide is in an antisense orientation relative to said regulatory region.

8. The nucleic acid construct of claim 5 wherein said heterologous polynucleotide is transcribed into an antisense RNA capable of inhibiting expression of a DNA methyltransferase.

9. The nucleic acid construct of claim 5 wherein said heterologous polynucleotide is transcribed into an interfering RNA.

10. The nucleic acid construct of claim 5 wherein said heterologous polynucleotide is transcribed into an interfering RNA that inhibits transcription of a DNA methyltransferase.

11. A transgenic plant or plant cell wherein said plant or plant cell comprises the nucleic acid of claim 1 operably linked to a heterologous polynucleotide.

12. The transgenic plant or plant cell of claim 11 wherein said heterologous polynucleotide comprises a nucleic acid sequence encoding a polypeptide.

13. The transgenic plant or plant cell of claim 11 wherein said heterologous polynucleotide is in an antisense orientation relative to said regulatory region.

14. The transgenic plant or plant cell of claim 11 wherein said heterologous polynucleotide is transcribed into an interfering RNA.

15. A method of producing a transgenic plant, said method comprising (a) introducing into a plant cell an isolated polynucleotide comprising the nucleic acid of claim 1 operably linked to a heterologous polynucleotide, and (b) growing a plant from said plant cell.

16. The method of claim 15 wherein said heterologous polynucleotide comprises a nucleic acid sequence encoding a polypeptide.

17. The method of claim 15 wherein said heterologous polynucleotide is in an antisense orientation relative to said regulatory region.

18. The method of claim 15 wherein said heterologous polynucleotide is transcribed into an interfering RNA.

* * * * *

SEQUENCE LISTING

```
<160> NUMBER OF SEQ ID NOS: 4

<210> SEQ ID NO 1
<211> LENGTH: 1836
<212> TYPE: DNA
<213> ORGANISM: Oryza sativa
<220> FEATURE:
<221> NAME/KEY: misc_feature
<222> LOCATION: (1)..(1836)
<223> OTHER INFORMATION: p530c10

<400> SEQUENCE: 1
gcctctcgac cacgagttta gcacttgtgc aacatatatg cgtgcgatga acatctactg      60
atgcgccatg cgaattttag cgttcgttca tgacgcttcc aacggcacag aggctgagca     120
gcagcatgca tgcatggctc ttgtgaaaac aaaaaaggtt actggtaaat gacatgctgc     180
tgtagctagc tagcagaatg caaggcccat gcatatgcaa tgctatgcga caagtacagt     240
accagcatgt atggtagcca gctaactaat ctatcagcag aggcagcaag ctcgtgcatg     300
gtgtgatgca cttctctcca gtaatctagt ggtaattttc acccaaagcg ttgctcatat     360
ggacagtaat tagtaatatt accaaggttc acaatcccgt tacctgacca aatactactc     420
acgaatggta tctctggttt tcgttaaaac cgttggtaaa ccagcaaaaa tagacaaaat     480
ttgtcaaaat tttaaatttt agttttttt ttttaactta gccgggaaac cttgaagttt     540
gtgctgtcga gctgtcctgg gaaggacggt tttggttggg attgtgaacc ctggttactg     600
cacttcattt ttgaacagat attagtgcaa cagacaaatg ccaacgcatt tttttctgtt     660
taccggcaag ctgaagcttt tacgatcccc atacagccgt tgctgcaaac ctgccaagaa     720
agagcagcag aaacaggtgt cattttgtgg tggaaagcca agtaaagtaa acagaagatg     780
gaagatagtg aggaccaggg agtgaggcag gggacacatg gcccacgcct ccctgcacat     840
tttcgtgtat aaatacaggt ggatgcatcg ctctcccagc atccatcggt tctctgctct     900
gttcatccat agagtttcct cctcttctcc tttagtgcaa ggtagagaag agcatgtgtg     960
tgtgtgtgtg tgtgtgaact gtgaagtgca gagtgcttct gtagttctgt gttatgtcca    1020
tagtgatctt gttaggattg ttgctatgga tgcatgatgt tatggttgat ctctgaatta    1080
cagtagggac ttttctgaga tctctggatt agtgggggt gctaaatttt ttctggttg     1140 catcagcttg ggtttctggt attggtgtgg gttcttgctc tgaattttgg ttcagaatgt    1200
```

-continued

| | |
|---|---|
| cgatttgttt gtgtttgttc tctgaagttg agagtagcta tgatccatcc agcacagaac | 1260 |
| tgcaggtcct gcctgccggc tgcatataca ggacatgcca ttttgcaagc tctgggctta | 1320 |
| tggtttctct tttggagttc ttcttcttgc atgatctgtg ttctctaaca aaggaagcaa | 1380 |
| gatttagcaa ctttattcag agacaagaaa aggatctggc aacctttgt ttctgttta | 1440 |
| tcctactcgt aaagattgtt atttaagcaa aaatttccca aaagttttaa atataatttc | 1500 |
| catgatgtgc cactctcatg tccttgaacc tggcactcat tatgggctcc tcagaagtgc | 1560 |
| tgtagctaat gtcactaatc tttttgtatct ttgttcatag tcttgtattt tatgatgctt | 1620 |
| atccctttgt gctttccatg tttgatgtcc aaatgtcatg gcaatgtttt tgacttctag | 1680 |
| taggggtttt agtaccttt tgttagataa gtacatccaa attctgttta tttattcaaa | 1740 |
| aatcattctg tttattcact gaaaacattt gtccattcaa tggactcata aactgtctgt | 1800 |
| gtttttcagg cttgaggatc catctagaag atagca | 1836 |

```
<210> SEQ ID NO 2
<211> LENGTH: 1826
<212> TYPE: DNA
<213> ORGANISM: Oryza sativa
<220> FEATURE:
<221> NAME/KEY: misc_feature
<222> LOCATION: (1)..(1826)
<223> OTHER INFORMATION: p530d

<400> SEQUENCE: 2
```

| | |
|---|---|
| cacgagttta gcacttgtgc aacatatatg cgtgcgatga acatctactg atgcgccatg | 60 |
| cgaattttag cgttcgttca tgacgcttcc aacggcacag aggctgagca gcagcatgca | 120 |
| tgcatggctc ttgtgaaaac aaaaaaggtt actggtaaat gacatgctgc tgtagctagc | 180 |
| tagcagaatg caaggcccat gcatatgcaa tgctatgcga caagtacagt accagcatgt | 240 |
| atggtagcca gctaactaat ctatcagcag aggcagcaag ctcgtgcatg gtgtgatgca | 300 |
| cttctctcca gtaatctagt ggtaattttc acccaaagcg ttgctcatat ggacagtaat | 360 |
| tagtaatatt accaaggttc acaatcccgt tacctgacca aatactactc acgaatggta | 420 |
| tctctggttt tcgttaaaac cgttggtaaa ccagcaaaaa tagacaaaat ttgtcaaaat | 480 |
| tttaaatttt agttttttt ttttaactta gccgggaaac cttgaagttt gtgctgtcga | 540 |
| gctgtcctgg gaaggacggt tttggttggg attgtgaacc ctggttactg cacttcattt | 600 |
| ttgaacagat attagtgcaa cagacaaatg ccaacgcatt tttttctgtt taccggcaag | 660 |
| ctgaagcttt tacgatcccc atacagccgt tgctgcaaac ctgccaagaa agagcagcag | 720 |
| aaacaggtgt catttgtgg tggaaagcca agtaaagtaa acagaagatg gaagatagtg | 780 |
| aggaccaggg agtgaggcag gggacacatg gcccacgcct ccctgcacat tttcgtgtat | 840 |
| aaatacaggt ggatgcatcg ctctcccagc atccatcggt tctctgctct gttcatccat | 900 |
| agagtttcct cctcttctcc tttagtgcaa ggtagagaag agcatgtgtg tgtgtgtgtg | 960 |
| tgtgtgaact gtgaagtgca gagtgcttct gtagttctgt gttatgtcca tagtgatctt | 1020 |
| gttaggattg ttgctatgga tgcatgatgt tatggttgat ctctgaatta cagtagggac | 1080 |
| ttttctgaga tctctggatt agtgggggt gctaaatttt tttctggttg catcagcttg | 1140 |
| ggtttctggt attggtgtgg gttcttgctc tgaattttgg ttcagaatgt cgatttgttt | 1200 |
| gtgtttgttc tctgaagttg agagtagcta tgatccatcc agcacagaac tgcaggtcct | 1260 |
| gcctgccggc tgcatataca ggacatgcca ttttgcaagc tctgggctta tggtttctct | 1320 |
| tttggagttc ttcttcttgc atgatctgtg ttctctaaca aaggaagcaa gatttagcaa | 1380 |

```
ctttattcag agacaagaaa aggatctggc aacctttgt ttctgtttta tcctactcgt    1440
aaagattgtt atttaagcaa aaatttccca aaagttttaa atataatttc catgatgtgc    1500
cactctcatg tccttgaacc tggcactcat tatgggctcc tcagaagtgc tgtagctaat    1560
gtcactaatc ttttgtatct ttgttcatag tcttgtattt tatgatgctt atccctttgt    1620
gctttccatg tttgatgtcc aaatgtcatg gcaatgtttt tgacttctag taggggtttt    1680
agtacctttt tgttagataa gtacatccaa attctgttta tttattcaaa aatcattctg    1740
tttattcact gaaaacattt gtccattcaa tggactcata aactgtctgt gttttcagg    1800 cttgaggatc catctagaag atagca                                          1826

<210> SEQ ID NO 3
<211> LENGTH: 1816
<212> TYPE: DNA
<213> ORGANISM: Oryza sativa
<220> FEATURE:
<221> NAME/KEY: misc_feature
<222> LOCATION: (1)..(1816)
<223> OTHER INFORMATION: p530e

<400> SEQUENCE: 3
gcacttgtgc aacatatatg cgtgcgatga acatctactg atgcgccatg cgaattttag     60
cgttcgttca tgacgcttcc aacggcacag aggctgagca gcagcatgca tgcatggctc    120
ttgtgaaaac aaaaaaggtt actggtaaat gacatgctgc tgtagctagc tagcagaatg    180
caaggcccat gcatatgcaa tgctatgcga caagtacagt accagcatgt atggtagcca    240
gctaactaat ctatcagcag aggcagcaag ctcgtgcatg gtgtgatgca cttctctcca    300
gtaatctagt ggtaattttc acccaaagcg ttgctcatat ggacagtaat tagtaatatt    360
accaaggttc acaatcccgt tacctgacca atactactc acgaatggta tctctggttt    420
tcgttaaaac cgttggtaaa ccagcaaaaa tagacaaaat ttgtcaaaat tttaaatttt    480 agttttttt ttttaactta gccgggaaac cttgaagttt gtgctgtcga gctgtcctgg    540
gaaggacggt tttggttggg attgtgaacc ctggttactg cacttcattt ttgaacagat    600
attagtgcaa cagacaaatg ccaacgcatt tttttctgtt taccggcaag ctgaagcttt    660
tacgatcccc atacagccgt tgctgcaaac ctgccaagaa agagcagcag aaacaggtgt    720
cattttgtgg tggaaagcca agtaaagtaa acagaagatg gaagatagtg aggaccaggg    780
agtgaggcag gggacacatg gcccacgcct ccctgcacat tttcgtgtat aaatacaggt    840
ggatgcatcg ctctcccagc atccatcggt tctctgctct gttcatccat agagtttcct    900
cctcttctcc tttagtgcaa ggtagagaag agcatgtgtg tgtgtgtgtg tgtgtgaact    960
gtgaagtgca gagtgcttct gtagttctgt gttatgtcca tagtgatctt gttaggattg   1020
ttgctatgga tgcatgatgt tatggttgat ctctgaatta cagtagggac ttttctgaga   1080
tctctggatt agtgggggt gctaaatttt tttctggttg catcagcttg ggtttctggt   1140
attggtgtgg gttcttgctc tgaattttgg ttcagaatgt cgatttgttt gtgtttgttc   1200
tctgaagttg agagtagcta tgatccatcc agcacagaac tgcaggtcct gcctgccggc   1260
tgcatataca ggacatgcca ttttgcaagc tctgggctta tggtttctct tttggagttc   1320
ttcttcttgc atgatctgtg ttctctaaca aaggaagcaa gatttagcaa ctttattcag   1380
agacaagaaa aggatctggc aacctttgt ttctgtttta tcctactcgt aaagattgtt   1440
atttaagcaa aaatttccca aaagttttaa atataatttc catgatgtgc cactctcatg   1500
```

| | |
|---|---|
| tccttgaacc tggcactcat tatgggctcc tcagaagtgc tgtagctaat gtcactaatc | 1560 |
| ttttgtatct ttgttcatag tcttgtattt tatgatgctt atccctttgt gctttccatg | 1620 |
| tttgatgtcc aaatgtcatg gcaatgtttt tgacttctag taggggtttt agtacctttt | 1680 |
| tgttagataa gtacatccaa attctgttta tttattcaaa aatcattctg tttattcact | 1740 |
| gaaaacattt gtccattcaa tggactcata aactgtctgt gttttttcagg cttgaggatc | 1800 |
| catctagaag atagca | 1816 |

<210> SEQ ID NO 4
<211> LENGTH: 1841
<212> TYPE: DNA
<213> ORGANISM: Artificial Sequence
<220> FEATURE:
<221> NAME/KEY: misc_feature
<222> LOCATION: (1)..(1841)
<223> OTHER INFORMATION: p530f

<400> SEQUENCE: 4

| | |
|---|---|
| tttttgcctc tcgaccacga gtttagcact tgtgcaacat atatgcgtgc gatgaacatc | 60 |
| tactgatgcg ccatgcgaat tttagcgttc gttcatgacg cttccaacgg cacagaggct | 120 |
| gagcagcagc atgcatgcat ggctcttgtg aaaacaaaaa aggttactgg taaatgacat | 180 |
| gctgctgtag ctagctagca gaatgcaagg cccatgcata tgcaatgcta tgcgacaagt | 240 |
| acagtaccag catgtatggt agccagctaa ctaatctatc agcagaggca gcaagctcgt | 300 |
| gcatggtgtg atgcacttct ctccagtaat ctagtggtaa ttttcaccca aagcgttgct | 360 |
| catatggaca gtaattagta atattaccaa ggttcacaat cccgttacct gaccaaatac | 420 |
| tactcacgaa tggtatctct ggttttcgtt aaaaccgttg gtaaaccagc aaaaatagac | 480 |
| aaaatttgtc aaaattttaa attttagttt tttttttta acttagccgg gaaaccttga | 540 |
| agtttgtgct gtcgagctgt cctgggaagg acggttttgg ttgggattgt gaaccctggt | 600 |
| tactgcactt cattttttgaa cagatattag tgcaacagac aaatgccaac gcatttttt | 660 |
| ctgtttaccg gcaagctgaa gcttttacga tccccataca gccgttgctg caaacctgcc | 720 |
| aagaaagagc agcagaaaca ggtgtcattt tgtggtggaa agccaagtaa agtaaacaga | 780 |
| agatggaaga tagtgaggac cagggagtga ggcaggggac acatggccca cgcctccctg | 840 |
| cacattttcg tgtataaata caggtggatg catcgctctc ccagcatcca tcggttctct | 900 |
| gctctgttca tccatagagt ttcctcctct tctcctttag tgcaaggtag agaagagcat | 960 |
| gtgtgtgtgt gtgtgtgtgt gaactgtgaa gtgcagagtg cttctgtagt tctgtgttat | 1020 |
| gtccatagtg atcttgttag gattgttgct atggatgcat gatgttatgg ttgatctctg | 1080 |
| aattacagta gggactttc tgagatctct ggattagtgg ggggtgctaa attttttct | 1140 |
| ggttgcatca gcttgggttt ctggtattgg tgtgggttct tgctctgaat tttggttcag | 1200 |
| aatgtcgatt tgtttgtgtt tgttctctga agttgagagt agctatgatc catccagcac | 1260 |
| agaactgcag gtcctgcctg ccggctgcat atacaggaca tgccattttg caagctctgg | 1320 |
| gcttatggtt tctcttttgg agttcttctt cttgcatgat ctgtgttctc taacaaagga | 1380 |
| agcaagattt agcaacttta ttcagagaca agaaaggat ctggcaacct tttgtttctg | 1440 |
| ttttatccta ctcgtaaaga ttgttattta agcaaaaatt tcccaaaagt tttaaatata | 1500 |
| atttccatga tgtgccactc tcatgtcctt gaacctggca ctcattatgg gctcctcaga | 1560 |
| agtgctgtag ctaatgtcac taatcttttg tatctttgtt catagtcttg tattttatga | 1620 |
| tgcttatccc tttgtgcttt ccatgtttga tgtccaaatg tcatggcaat gttttttgact | 1680 |

```
tctagtaggg gttttagtac cttttttgtta gataagtaca tccaaattct gtttatttat    1740
tcaaaaatca ttctgtttat tcactgaaaa catttgtcca ttcaatggac tcataaactg    1800
tctgtgtttt tcaggcttga ggatccatct agaagatagc a                        1841
```